United States Patent [19]

Castello

[11] Patent Number: 4,931,051

[45] Date of Patent: Jun. 5, 1990

[54] WETNESS INDICATOR

[75] Inventor: Gregory L. Castello, Gilroy, Calif.

[73] Assignee: Edge Enterprises, Inc., Gilroy, Calif.

[21] Appl. No.: 12,110

[22] Filed: Feb. 6, 1987

[51] Int. Cl.$^5$ .............................................. A61F 13/16
[52] U.S. Cl. .................................................. 604/361
[58] Field of Search ................... 604/361, 362; 73/73; 116/206

[56] References Cited

U.S. PATENT DOCUMENTS

| | | | |
|---|---|---|---|
| 2,249,867 | 7/1941 | Snelling | 116/206 |
| 2,681,032 | 6/1954 | Shaw | 604/361 |
| 3,121,615 | 2/1964 | Price | 73/73 |
| 3,499,316 | 3/1970 | Krause | 116/206 |
| 3,675,654 | 7/1972 | Baker et al. | 604/361 |
| 3,731,685 | 5/1973 | Eidus | 604/361 |
| 3,759,261 | 9/1973 | Wang | 604/361 |
| 3,881,873 | 5/1975 | Klowden | 116/206 |
| 3,951,098 | 4/1976 | Meyers | 73/73 |
| 3,952,746 | 4/1976 | Summers | 604/361 |
| 4,022,211 | 5/1977 | Timmons et al. | 604/361 |
| 4,129,311 | 3/1980 | Felfoldi | 604/361 |
| 4,184,445 | 1/1980 | Burrows | 116/206 |
| 4,231,370 | 11/1980 | Mroz et al. | 116/206 |
| 4,287,153 | 9/1981 | Townsend | 604/361 |
| 4,327,731 | 5/1982 | Powell | 604/361 |
| 4,507,121 | 3/1985 | Leung | 604/361 |

FOREIGN PATENT DOCUMENTS 1433415  4/1976  United Kingdom ................ 604/361

Primary Examiner—C. Fred Rosenbaum
Assistant Examiner—Sharon Rose
Attorney, Agent, or Firm—William C. Milks, III

[57] ABSTRACT

A wetness indicator used on absorbent pads such as diapers for visually signalling the presence of water. The wetness indicator preferably comprises a hydratable salt mixture applied to a water permeable membrane and visible from an external observation of the absrobent pad. The hydratable salt has the characteristic of changing from the color it exhibits in its normal, anhydrous state to a contrasting color when it becomes hydrated. The wetness indicator is physically disposed within the pad so that it contacts water as it reaches the absorbent layers of the pad. The wetness indicator is constructed so that the hydratable salt mixture does not leach back into the absorbent layer or into contact with the wearer of the pad. The hydratable salt may be arranged to combine with a binder upon hydration to reduct toxicity.

47 Claims, No Drawings

WETNESS INDICATOR

BACKGROUND OF THE INVENTION

This invention relates to wetness indicators used with absorbent products such as disposable diapers and the like.

A number of wetness indicators has been disclosed in the prior art for use on absorbent pad assemblies such as disposable diapers. With the development of increasingly improved materials to absorb and direct wetness away from the baby's body and into the absorbent layers of a diaper, it has become increasingly difficult for a parent to be able to tell when a diaper is wet by touching the interior diaper surface. Due to the improved absorbent layers, parents often allow an infant to completely saturate a diaper before changing the diaper. As a result, a period of time sufficient for bacteria to grow often elapses, and diaper rash often ensues. Therefore, it would be highly desirable to provide a disposable diaper having a wetness indicator which immediately signals wetness within the absorbent layers.

A number of differing compositions or methods of construction has been suggested for indicating that a diaper is wet. For instance, U.S. Pat. No. 4,231,370 to Mroz et al. discloses a pH change/color change wetness indicator which is a solid mixture dispersed in an adhesive. U.S. Pat. No. 4,022,211 to Timmons et al. discloses a water soluble coloring agent which is visible when the diaper is dry, but which disappears when the diaper becomes wet. U.S. Pat. No. 3,952,746 to Summers discloses the use of humidity indicator paper mounted on an absorbent area of the diaper. U.S. Pat. No. 4,327,731 to Powell discloses moisture activated enzymatic systems and chromogens or pigment producing agents used as wetness detectors. U.S. Pat. Nos. 3,759,261 to Wang and 4,192,311 to Felfoldi disclose masked color layers which become visible when intervening layers become wet.

It is unnecessary for a diaper wetness indicator to indicate pH. Many pH indicators have proven to be unreliable. Multi-layered masking systems prove to be somewhat ineffective. An inexpensive, non-toxic, simple composition signalling the presence of water as a wetness indicator would be advantageous.

SUMMARY OF THE INVENTION

The present invention provides a wetness indicator that includes a hydratable salt as an active ingredient to detect and visually signal the presence of water. In a preferred embodiment, the hydratable salt is bound to a membrane for attachment to diapers and other like products.

The hydratable salt must be present along the membrane in a concentration sufficient to exhibit a first color when the diaper or other product to which the indicator is mounted is in an anhydrous or dry condition. When the indicator becomes wet, or attains a hydrated condition, the hydratable salt causes the wetness indicator to exhibit a second color which is substantially in contrast to the first color.

Care must be taken that the indicator compounds be substantially non-toxic both in the anhydrous and hydrated condition. Although a number of hydratable salt compounds would be acceptable, the preferred embodiment discloses the use of copper sulfate which changes from white to a very distinct bright azure blue color. Other satisfactory hydratable salts are cobalt salts, such as cobalt nitrate and ferrous or ferric salts.

A number of techniques may be used to mechanically incorporate the wetness indicator into the diaper or absorbent pad structure. The wetness indicator may be combined with a water soluble binder material such as polyethylene glycol or applied directly to a paper binder and mounted beneath a plastic liner to be placed against the exterior absorbent layer surface of the diaper. For purposes of easy visibility, the wetness indicator should be disposed along the outer surface of the diaper for viewing through a transparent or at least translucent liner layer.

BRIEF DESCRIPTION OF THE DRAWINGS

FIG. 1 is a partial rear view of one embodiment of a diaper structure of the invention shown in place on the torso of a child and showing wetness indicator stripes;

FIG. 2 is a planar view of a portion of a disposable diaper structure in which the wetness indicator is provided in a random pattern on the diaper surface;

FIG. 3 is a cross-sectional detailed view of an absorbent pad incorporating the wetness indicator of the present invention; and FIG. 4 is a schematic illustration of a layered construct for the wetness indicator.

DESCRIPTION OF THE PREFERRED EMBODIMENTS

Referring to FIG. 1 of the drawings, there is shown a striped embodiment of the present invention as worn on the torso of a child or infant. In this particular embodiment, the wetness indicator is embossed onto the diaper surface as a series of vertical parallel stripes 100, which are centered along the crotch region of the diaper.

A second embodiment of the invention is shown in FIG. 2. The wetness indicator of this version of the invention takes the form of an ornamental printed design or pattern 150 interspersed about the exterior surface of the prefolded, triangular diaper.

The major components of an exemplary diaper structure 160 is shown in FIG. 3. A thin, moisture porous wicking layer 170 is provided along the surface of diaper 160 intended to contact the baby's skin, herein designated as the inner surface of the diaper. The wicking layer assists in drawing or "wicking" the acidic urine away from the baby's skin for absorption and retention in the absorbent layer. Bonded to the outer surface of wicking layer 170 is the inner surface of an absorbent layer 180. The absorbent layer 180 is constructed from any suitable material such as wood pulp fibers, cotton, or synthetic "super-absorbent" materials. The outermost layer of the typical diaper consists of a thin, usually plastic, moisture-impervious liner layer 190. Liner layer 190 is preferably constructed from a translucent or transparent material such as polyethylene film.

The wetness indicator 200 must be disposed within the diaper structure such that it is in liquid communication with the absorbent layer 180. For the preferred embodiment shown in FIG. 3, the wetness indicators 200 are sandwiched between the outer surface of absorbent layer 180 and the inner surface of liner layer 190.

Other arrangements in which the wetness indicators are not in direct contact with the absorbent layer are also contemplated. For instance, the wetness indicators might be located along the outside surface of the moisture-proof liner layer 190. Strings or wicks originating in the absorbent layer and threaded through the liner layer could be provided to conduct the fluid to trigger a color change in the indicator.

The wetness indicators must be plainly visible from the exterior of the diaper. If a translucent material is used for the liner layer, the wetness indicator sandwiched beneath such layer must exhibit a color change sufficiently dramatic to be read either through the liner layer or be provided with a transparent window. Transparent windows may be located at the wetness indicator locations, or the entire liner layer could be formed from a transparent material. The wetness indicators might also be incorporated into the liner layer itself. The wetness indicators might be separately assembled and spliced to portions of the liner layer in stripes as shown in FIG. 1. To assist in the detection of the color change, areas surrounding the windows could be pre-dyed in the color of the hydrated compound so that the indicator would change colors to match the pre-dyed areas. In this way, the person checking would feel more confident that the appropriate color change had taken place.

The wetness indicators may be manufactured and assembled separately in indicator assemblies which are then arranged along the partly constructed diaper structure. It is essential that none of the hydratable salt components of the wetness indicators "bleed" out of the indicator assemblies onto the other portions of the diaper or into contact with the wearer's skin. For instance, a cellulose phosphate paper may be used to prevent the copper compound from soaking through the indicator assembly to contact the skin of the wearer.

Safety considerations in constructing absorbent pads for use by infants or patients unable to care for themselves requires that the wetness indicators be substantially non-toxic in the event of ingestion. Therefore, the wetness indicators must be substantially non-toxic in both the anhydrous and hydrated forms.

The active component of the wetness indicator is a hydratable salt which undergoes a color change when it transforms from an anhydrous compound to a hydrated compound. The salt must be able to be stored in the wetness indicator form for long periods of time and be able to withstand ambient air humidity without undergoing the color change.

The color change must be drastic and unambiguous so as to clearly indicate that the diaper has become wet. Normal perspiration by the wearer should also be tolerated by the wetness indicator without triggering the color change. The most obvious changes to read are changes from a colorless compound to a colored compound or from a white compound to a contrasting colored compound.

Copper sulfate has been found to be one hydratable salt which is especially suitable for use in the present invention. In its anhydrous condition, it is a white powder with a slightly gray cast, depending on the exact formulation. When copper sulfate contacts water, it transforms into a contrasting-colored hydrated compound which is a relatively bright azure blue in color. Cupric sulfate is extremely hygroscopic in its anhydrous salt state.

Copper sulfate, as the exemplary color indicator, is preferably added to the water soluble binder material, such as polyethylene glycol, while in its liquid state. This mixture can then be directly applied to the absorbent pad in the desired configuration (i.e. stripes, patterns, etc.).

The wetness indicator 200 may also be constructed in a layered fashion. The water soluble polymer polyethylene glycol is available in a variety of molecular weights. The higher molecular weight compounds display higher melting points and dissolve more slowly in water. The wetness indicator can be constructed with layers of polyethylene glycol arranged so that the copper sulfate is mixed with the lowest molecular weight polyethylene glycol and layered over a layer of higher molecular weight polyethylene glycol. Below the higher molecular weight layer is a layer of binder material consisting of either sodium polysulfide, Amberlite or cellulose phosphate powder. Amberlite is a type of ion exchange resin found to be suitable as a binder. As the polymer layers dissolve (lowest first to show color change) the $CuSO_4$ comes into contact with sodium polysulfide or Amberlite or cellulose phosphate to result in a compound of lower toxicity to humans.

If sodium polysulfide is chosen as the binder, an insoluble precipitate is formed. If Amberlite is used, it results in an insoluble resin which chelates insoluble copper ions. Cellulose phosphate powder results in an insoluble complex molecule.

A number of reactions take place simultaneously:

(1) $CuSO_4 + H_2O$ (white) $\rightarrow CuSO_4.5H_2O$ (blue copper pentahydrate).
(2) $CuSO_4 + NH_3 + H_2O \rightarrow Cu(NH_3)_4SO_4.H_2O$ (deep blue).
(3) $CuSO_4.5H_2O + NH_3 \rightarrow Cu(NH_3)_4SO_4.H_2O$ (deep blue)
(4) $CuSO_4.5H_2O$ + sodium polysulfide $\rightarrow$ CuS.
(5) $Cu(NH_3)_4SO_4.H_2O$ + sodium polysulfide $\rightarrow$ CuS (black).

Reaction 1: The blue color becomes apparent due to a shift in bond energy from the ultraviolet (vacuum) to the ultraviolet (visible) range of the electromagnetic spectrum. Ultraviolet in the visible range expresses wavelengths falling in the range of 200 to 800 nanometers. Copper sulfate is also substantially non-toxic in the amounts required.

Reactions 2 and 3: The formation of a tetra amino copper sulfate complex. This is favored when free ammonia is present. Any free ammonia found in urine will produce the tetra amine complex. It has bond energies close in range to but more stable than the pentahydrate. The pentahydrate from reaction 1 dominates in concentration due to the greater concentration of water versus the concentration of free ammonia in urine. The bond wavelengths increase slightly, producing a richer, deeper blue response in the visible ultraviolet spectrum. The higher stability of the molecules results in an acceptable toxicity to humans because of the lessened availability of ions that compose the molecule in the amounts required.

Reactions 4 and 5: The products from reactions 1 through 3 when contacted with the sodium polysulfide yields a non-toxic, black colored compound, copper sulfide. When sodium polysulfide is contacted with the copper sulfate in its salt forms and exposed to urine, the products of reactions 1 through 3 are likely intermediates in the formation of a very insoluble copper sulfide. This insolubility is the reason for the low toxicity of copper sulfide. A concentrated acid is required to ionize CuS. In the event of ingestion by a human, the digestive tract environment is not acidic enough in concentration to ionize CuS. If consumed, the CuS is not absorbable and passes through the digestive tract and out of the body.

Reactions 1 through 3 are very fast to react to moisture, while reaction 4 has slower kinetics unless in a liquid phase. As time passes, once the wetness indicator has been wetted, the reaction site becomes liquid. The active ingredients then turn from azure blue to a deeper blue and eventually turn black.

To prevent the anhydrous copper sulfate from reacting with environmental humidity, an osmotic membrane which only permits liquid phase water to pass through it may be used to provide a barrier between the salt and any vapor phase water. An example of a suitable osmotic membrane is the Filmtec ® FT-30 membrane, available from Filmtec of Minneapolis, Minn. Another suitable material is Whatman P-81 chromatography paper.

From the layered construction of the wetness indicator, premature hydration may be prevented by laminating over the layer of low molecular weight polyethylene glycol combined with copper sulfate with a thin coat or layer of a slightly higher molecular weight polyethylene glycol. These layers could then be directly applied to cellulose phosphate paper or used with a binder layer as previously discussed.

Although the copper sulfate may be used in its dry, powdered form, it is advantageous for manufacturing purposes to apply copper sulfate as a polymer-combined compound to a membrane or support member.

The polymer acts as the host which makes the wetness color indicator easier to handle, while the binder material acts to lower the toxicity of the hydrated compounds. The support member serves to carry the wetness indicator for attachment to the absorbent pad and to prevent leakage of the compounds. FIG. 4 summarizes schematically the layered construction of a wetness indicator constructed in accordance with this invention.

Layer A is the copper sulfate compound combined with a polymer such as polyethylene glycol. The molecular weight of this layer of polymer is the lowest. This polymer is more readily soluble making water more available to the anhydrous salt. Layer B is a layer of slightly higher molecular weight polyethylene glycol, for example a molecular weight of 1000, combined with the binder material (i.e. sodium polysulfide or amberlite or cellulose phosphate powder). Layer C, the outermost layer, is another layer of the highest molecular weight polymer (i.e. polyethylene glycol having an MW of 1500) which contacts the support member 220 (i.e. cellulose phosphate filter paper or an osmotic membrane).

This construction can be manufactured by a variety of methods. The liquid copper sulfate/polymer compound can be allowed to harden separately in molds to be removed later, or the layers can be directly applied to the support member in liquid form one at a time and allowed to harden before the application of a subsequent layer. The prefabricated wetness indicators can then be mechanically incorporated into the structure of the absorbent pad.

The wetness indicator could also be produced in a strip where the mixed hydratable salts are placed in the central area of an osmotic membrane using a water soluble adhesive. A transparent film such as polypropylene could then be sealed to the strip along the perimeter surrounding the copper sulfate using a non-water soluble glue. Thus, moisture could pass through the osmotic membrane to trigger the color change, but the copper sulfate would remain trapped between the osmotic membrane and the transparent liner layer.

As an alternative method of manufacture, the hydratable salt mixture could be mixed in an anhydrous alcohol such as methanol and applied to a membrane, with the alcohol evaporating away. An insoluble glue could then be used to secure the treated indicator membrane to the appropriate location on the absorbent pad or diaper.

The foregoing is a complete description of the invention, but is not intended to limit the scope of the invention, except as stated in the appended claims. While the above provides a full and complete disclosure of the preferred embodiment of the invention, various modifications, alternate constructions, and equivalents may be employed without departing from the true spirit and scope of the invention.

For example, the embodiment described herein discloses a diaper in which only discrete portions of the absorbent pad or diaper are provided with wetness indicators. It is conceivable that in some applications, the entire absorbent area could be provided with the wetness indicator. Therefore, the above description and illustrations should not be construed as limiting the scope of the invention which is defined by the appended claims.

What is claimed is:

1. An article configured to be worn in intimate contact with a living being near a source of aqueous excretions from the being comprising:
   an absorbent layer comprising a water absorbent material in liquid communication with the source; and
   a hydratable salt comprising a transition metal radical, the salt being in liquid communication with the absorbent layer, the salt being characterized by a first color in an unhydrated physical state and the salt being responsive to liquid phase water present in the aqueous excretion absorbed into the absorbent layer for transitioning from the unhydrated physical state to a hydrated physical state characterized by a second color, the salt being present in a concentration sufficient to produce a humanly perceptible color change, the color change occurring independent of the salinity of the excretion.

2. The article of claim 1, further comprising a water permeable membrane between the absorbent layer and the hydratable salt in liquid communication with the absorbent layer and the salt and a liner overlaid over said hydratable salt.

3. The article of claim 2, wherein said liner is constructed from a water impermeable plastic material.

4. The article of claim 1, wherein said hydratable salt comprises a cupric salt.

5. The article of claim 4, wherein said hydratable salt comprises copper sulfate.

6. The article of claim 1, wherein said hydratable salt comprises a cobalt salt.

7. The article of claim 1, wherein said hydratable salt comprises a ferrous salt.

8. The article of claim 1, wherein said hydratable salt comprises a ferric salt.

9. The article of claim 1, wherein said amount of said hydratable salt is substantially non-toxic.

10. The article of claim 2, wherein said hydratable salt is in powder form and sealed between said liner and said absorbent layer.

11. The article of claim 2, wherein said water permeable membrane comprises an osmotic membrane.

12. The article of claim 1, wherein said hydratable salt is combined with a water soluble polymer.

13. The article of claim 12, wherein said water soluble polymer is polyethylene glycol.

14. The article of claim 1, wherein said hydratable salt is combined with polyethylene oxide.

15. The article of claim 2, wherein said hydratable salt is combined with a water soluble adhesive and applied to said water permeable membrane.

16. The article of claim 2, wherein said water permeable membrane comprises chromatography paper.

17. The article of claim 2, wherein said liner comprises a transparent plastic sealant.

18. The article of claim 2, wherein said liner comprises polypropylene film.

19. The article of claim 2, wherein said hydratable salt is combined with an anhydrous alcohol prior to application onto said first side of said water permeable membrane.

20. The article of claim 19, wherein said anhydrous alcohol is methanol.

21. The article of claim 2, wherein said water permeable membrane comprises a layer of water soluble polymer.

22. The article of claim 21, wherein said polymer comprises polyethylene glycol.

23. The article of claim 1, wherein the hydratable salt is combined with a first polymer which is water soluble and has a first molecular weight to form a first layer, and further comprising:
a second layer composed of a binder, the binder being combined with a second polymer which is water soluble and has a second molecular weight; and
a support layer on which the first layer and the second layer are respectively deposited, the support layer being in liquid communication with the absorbent layer.

24. The article of claim 23, wherein said second molecular weight is higher than said first molecular weight.

25. The article of claim 23, wherein said hydratable salt comprises a cupric salt.

26. The article of claim 25, wherein said cupric salt comprises copper sulfate.

27. The article of claim 23, wherein said hydratable salt comprises a cobalt salt.

28. The article of claim 23, wherein said hydratable salt comprises a ferrous salt.

29. The article of claim 23, wherein said hydratable salt comprises a ferric salt.

30. The article of claim 23, wherein said first and second polymers comprise polyethylene glycol.

31. The article of claim 23, wherein said binder comprises sodium polysulfide.

32. The article indicator of claim 23, wherein said binder comprises an ion exchange resin.

33. The article wetness indicator of claim 23, wherein said binder comprises cellulose phosphate powder.

34. The article indicator of claim 23, further comprising a sealant layer overlying said first layer.

35. The article wetness indicator of claim 34, wherein said sealant layer comprises a thin film of a low molecular weight polymer.

36. The article of claim 35, wherein said low molecular weight polymer comprises polyethylene glycol.

37. The article of claim 23, wherein said support layer comprises cellulose phosphate filter paper.

38. The article of claim 23, wherein said support layer comprises an osmotic membrane.

39. A liquid phase water indicating disposable diaper for collecting and absorbing moisture, comprising:
an absorbent layer having an inner surface and an outer surface;
a liner layer adherently disposed along said outer surface of said absorbent layer; and
a wetness indicator disposed in the crotch region of said diaper, said wetness indicator interposed between said absorbent layer and said liner layer so as to be visible through said liner layer, said wetness indicator in fluid communication with said absorbent layer, said wetness indicator comprising:
a hydratable salt present in an amount sufficient to exhibit a first color when in an anhydrous condition and a second color when in a hydrated condition, said hydratable salt being substantially non-toxic in both the anhydrous and hydrated conditions, and further wherein said first color is substantially in contrast to said second color.

40. The disposable diaper of claim 39, wherein said hydratable salt comprises a cobalt salt.

41. The disposable diaper of claim 39, wherein said hydratable salt comprises a ferrous salt.

42. The disposable diaper of claim 39, wherein said hydratable salt comprises a ferric salt.

43. The disposable diaper of claim 39, further comprising an osmotic membrane permitting fluid to flow from said absorbent layer through said osmotic membrane to contact said hydratable salt and preventing said hydratable salt from passing through said osmotic membrane to said absorbent layer.

44. The disposable diaper of claim 39, wherein said liner layer is transparent.

45. The disposable diaper of claim 39, wherein said wetness indicator is visible through a window and further wherein said window is surrounded by a region pre-dyed to the color of the hydrated hydratable salt.

46. A liquid phase water indicating disposable diaper for collecting and absorbing moisture, comprising:
an absorbent layer having an inner surface and an outer surface;
a liner layer adherently disposed along said outer surface of said absorbent layer; and
a wetness indicator disposed along a diaper surface in a random pattern, said wetness indicator interposed between said absorbent layer and said liner layer so as to be visible through said liner layer, said wetness indicator in fluid communication with said absorbent layer, said wetness indicator comprising:
a hydratable salt present in an amount sufficient to exhibit a first color when in an anhydrous condition and a second color when in a hydrated condition, said hydratable salt being substantially non-toxic in both the anhydrous and hydrated conditions, and further wherein said first color is substantially in contrast to said second color.

47. A liquid phase water indicating disposable diaper for collecting and absorbing moisture, comprising:
an absorbent layer having an inner surface and an outer surface;
a liner layer adherently disposed along said outer surface of said absorbent layer; and
a wetness indicator disposed along a diaper surface in stripes extending from a front portion of said diaper towards a back portion of said diaper, said wetness indicator interposed between said absorbent layer and said liner layer so as to be visible through said liner layer, said wetness indicator in fluid communication with said absorbent layer, said wetness indicator comprising:
a hydratable salt present in an amount sufficient to exhibit a first color when in an anhydrous condition and a second color when in a hydrated condition, said hydratable salt being substantially non-toxic in both the anhydrous and hydrated conditions, and further wherein said first color is substantially in contrast to said second color.

* * * * *